United States Patent [19]

Bierman

[11] Patent Number: 5,722,959

[45] Date of Patent: Mar. 3, 1998

[54] CATHETER SECUREMENT DEVICE

[75] Inventor: Steven F. Bierman, Del Mar, Calif.

[73] Assignee: Venetec International, Inc., Mission Viejo, Calif.

[21] Appl. No.: 601,622

[22] Filed: Feb. 14, 1996

Related U.S. Application Data

[60] Provisional application No. 60/006,029, Oct. 24, 1995.

[51] Int. Cl.$^6$ ..................................................... A61M 5/32
[52] U.S. Cl. ................................ 604/174; 128/DIG. 26
[58] Field of Search ............................... 604/174, 178, 604/179, 180, 165; 128/DIG. 26

[56] References Cited

U.S. PATENT DOCUMENTS

| | | |
|---|---|---|
| 2,525,398 | 2/1950 | Collins . |
| 2,533,961 | 12/1950 | Rousseau et al. . |
| 3,167,072 | 1/1965 | Stone et al. . |
| 3,856,020 | 12/1974 | Kovac . |
| 3,900,026 | 8/1975 | Wagner . |
| 3,906,946 | 9/1975 | Nordstrom . |
| 3,973,565 | 8/1976 | Steer . |
| 4,082,094 | 4/1978 | Dailey . |
| 4,114,618 | 9/1978 | Vargas . |
| 4,129,128 | 12/1978 | McFarlane . |
| 4,161,177 | 7/1979 | Fuchs . |
| 4,224,937 | 9/1980 | Gordon ........................... 604/180 |
| 4,250,880 | 2/1981 | Gordon ........................... 604/180 |
| 4,316,461 | 2/1982 | Marais et al. . |
| 4,326,519 | 4/1982 | D'Alo et al. . |
| 4,362,156 | 12/1982 | Feller, Jr. et al. . |
| 4,480,639 | 11/1984 | Peterson et al. . |
| 4,633,863 | 1/1987 | Filips et al. . |
| 4,711,636 | 12/1987 | Bierman ........................... 604/180 |
| 4,852,844 | 8/1989 | Villaveces . |
| 4,857,058 | 8/1989 | Payton . |
| 4,863,432 | 9/1989 | Kvalo . |
| 4,898,587 | 2/1990 | Mera . |
| 4,997,421 | 3/1991 | Palsrok et al. . |
| 5,037,397 | 8/1991 | Kalt et al. . |
| 5,084,026 | 1/1992 | Shapiro ........................... 604/179 |
| 5,192,274 | 3/1993 | Bierman ........................... 604/180 |
| 5,342,317 | 8/1994 | Claywell . |
| 5,344,406 | 9/1994 | Spooner . |
| 5,346,479 | 9/1994 | Schneider . |
| 5,352,211 | 10/1994 | Merskelly . |
| 5,354,282 | 10/1994 | Bierman ........................... 604/174 |
| 5,354,283 | 10/1994 | Bark et al. . |
| 5,382,239 | 1/1995 | Orr et al. . |
| 5,413,562 | 5/1995 | Swauger ........................... 604/179 |
| 5,449,349 | 9/1995 | Salles et al. . |
| 5,468,228 | 11/1995 | Gebert . |
| 5,496,283 | 3/1996 | Alexander . |
| 5,520,656 | 5/1996 | Byrd . |
| 5,522,803 | 6/1996 | Teissen-Simony . |
| 5,527,293 | 6/1996 | Zamierowski . |

FOREIGN PATENT DOCUMENTS

| | | |
|---|---|---|
| 20247590 | 12/1987 | European Pat. Off. . |
| 2341297 | 8/1973 | Germany . |
| 2063679 | 11/1980 | United Kingdom . |
| WO80/01458 | 7/1980 | WIPO . |
| WO92/19309 | 11/1992 | WIPO . |

*Primary Examiner*—Sam Rimell
*Assistant Examiner*—Luke Yeh
*Attorney, Agent, or Firm*—Knobbe, Martens, Olson & Bear, LLP

[57] ABSTRACT

A securement device retains an indwelling catheter at a desired incident angle while allowing incremental adjustments of the incident angle without disconnecting the catheter from the retainer. The retainer includes an arcuate slot which curves in a direction toward an insertion site of the indwelling catheter. The slot receives a portion of a hub of the catheter. Movement of the catheter hub along the arcuate path defined by the slot changes the incident angle of the catheter. The retainer also includes protrusions which project into the slot and capture a hub of the catheter at discrete positions within the slot. These positions correspond to commonly desired incident angles of the catheter for given medical applications. The retainer also connects to an anchoring base in order to secure the retainer to the patient's skin proximate to the catheterization site.

48 Claims, 5 Drawing Sheets

CATHETER SECUREMENT DEVICE

RELATED CASE

The present application claims the benefit under 35 U.S.C. §119(e) of provisional application Ser. No. 60/006,029, filed Oct. 24, 1995.

BACKGROUND OF THE INVENTION

1. Field of the Invention

The present invention relates in general to a catheterization device. In particular, the present invention relates to a securement device for a catheter or a like article.

2. Description of Related Art

Medical treatment of patients commonly involves the use of percutaneously inserted catheters to direct fluids directly into the bloodstream, a specific organ or an internal location of the patient, or to monitor vital functions of the patient. For instance, intraarterial catheters are commonly used to monitor vital functions or to sample arterial blood for analyzing blood oxygen levels or performing other types of blood work.

In common practice, a health care provider, such as, for example, a nurse or doctor (for ease of description, as used herein the term "health care provider" will refer to health care providers generally and will not be restrictive in meaning), uses adhesive or surgical tape to maintain the catheter in place on the skin of the patient. The connection between a fluid tubing and the catheter is likewise maintained by tape.

In intraarterial applications, the depth of the artery causes the indwelling catheter to project into the skin at a steeper angle than with intravenous applications. In practice, an incident angle formed between the catheter and the patient's skin generally ranges between 7° and 15°, although some applications produce incident angles within a larger range (e.g., 0° to 30°).

To support the catheter at a desired incident angle, a health care provider commonly positions a piece of folded gauze beneath the hub of the indwelling catheter. Tape is used to secure the gauze and catheter in place.

Intraarterial catheters used in monitoring patient vital functions often are position sensitive because of the transducers used therewith. That is, the performance or operation of the monitoring device is significantly impacted by the position of the indwelling catheter. The depth of an artery also can change with movement of the patient's wrist. A health care provider therefore tends to adjust the catheter incident angle during the course of the patient's treatment. This procedure involves removing the tape and gauze and retaping another gauze pad, which the health care provider folds to a different thickness, under the catheter hub.

The gauze used to establish the catheter incident angle commonly absorbs blood and other fluids thereby becoming dirty and unsterile. The tape and the gauze also tend to cover the catheterization site (i.e., the cannula insertion point). The health care provider therefore must remove the tape and gauze to replace the soiled gauze or to inspect the insertion point for inflammation or infection, and must then replace the gauze and retape the catheter.

The entire taping procedure takes several minutes of the valuable time of the health care provider. Health care providers also tend to remove their gloves when taping because most health care providers find such taping procedures difficult and cumbersome when wearing gloves. Thus, a great deal of valuable time is spent applying significant amounts of surgical tape to indwelling catheters and readjusting the incident angle of the catheter during these procedures. The frequent application and removal of surgical tape also commonly results in the excoriation of the skin of the patient in the area of the insertion.

In addition, establishing the incident angle of the indwelling catheter using folded pieces of gauze inherently results in a less than constant incident angle being achieved. The resultant gauze shim positioned under the catheter hub tends to slip, thereby changing the catheter incident angle over time.

SUMMARY OF THE INVENTION

A need therefore exists for a securement device for an indwelling catheter which allows for easy adjustment of the catheter incident angle while securely fixing the catheter at a desired incident angle once set by a health care provider.

One aspect of the present invention involves a securement device for securing an indwelling catheter to a patient's skin. The securement device comprises a retainer having an arcuate slot sized to receive a portion of a catheter hub. The slot extends away from the patient's skin with the retainer coupled to the skin of the patient and curves toward an insertion site of the indwelling catheter. The slot is contoured to retain the portion of the hub at a plurality of positions relative to the patient's skin.

In accordance with another aspect of the present invention, a securement device is provided for securing a catheter to a patient's skin. The catheter includes a hub which has at least generally opposing grooves that extend transversely to a longitudinal axis of the catheter. The securement device comprises a base coupled to an adhesive surface and a retainer coupled to the base by cooperating, interengaging structure between the base and the retainer. The retainer also includes a pair of opposing, arcuate rails which project above the base in a direction generally transverse to the base. Each rail extends along an arc. The arc is defined within a plane which is positioned generally transverse to the base and is generally parallel to the longitudinal axis of the catheter. Each rail also is sized to fit within a corresponding groove of the catheter hub. The rails include at least one pair of corresponding protrusions which project toward each other to decrease a distance between the rails. The distance between the protrusions is less than the distance between the grooves of the catheter hub.

An additional aspect of the present invention involves a securement device for securing an indwelling catheter to a patient's skin. The catheter includes a hub. The securement device comprises a base coupled to an adhesive surface and a retainer coupled to the base by cooperating, interengaging structure between the base and the retainer. The retainer includes means for retaining the hub of the catheter in at least two positions relative to the base with an incident angle of the indwelling catheter varying between the positions.

A preferred method of adjusting an incident angle of an indwelling catheter involves providing a retainer having an arcuate slot which curves in a direction toward the insertion site of the indwelling catheter. A portion of a hub of the catheter is positioned within the slot. The catheter hub is secured in a first position within the slot to establish a first incident angle of the catheter. Sliding the catheter hub within the slot along the arcuate path defined by the slot changes the incident angle of the catheter. The catheter hub is secured in a second position within the slot to establish a second incident angle of the catheter.

BRIEF DESCRIPTION OF THE DRAWINGS

These and other features of the invention will now be described with reference to the drawings of a preferred embodiment which is intended to illustrate and not to limit the invention, and in which.

DETAILED DESCRIPTION OF A PREFERRED EMBODIMENT

Figure 1:
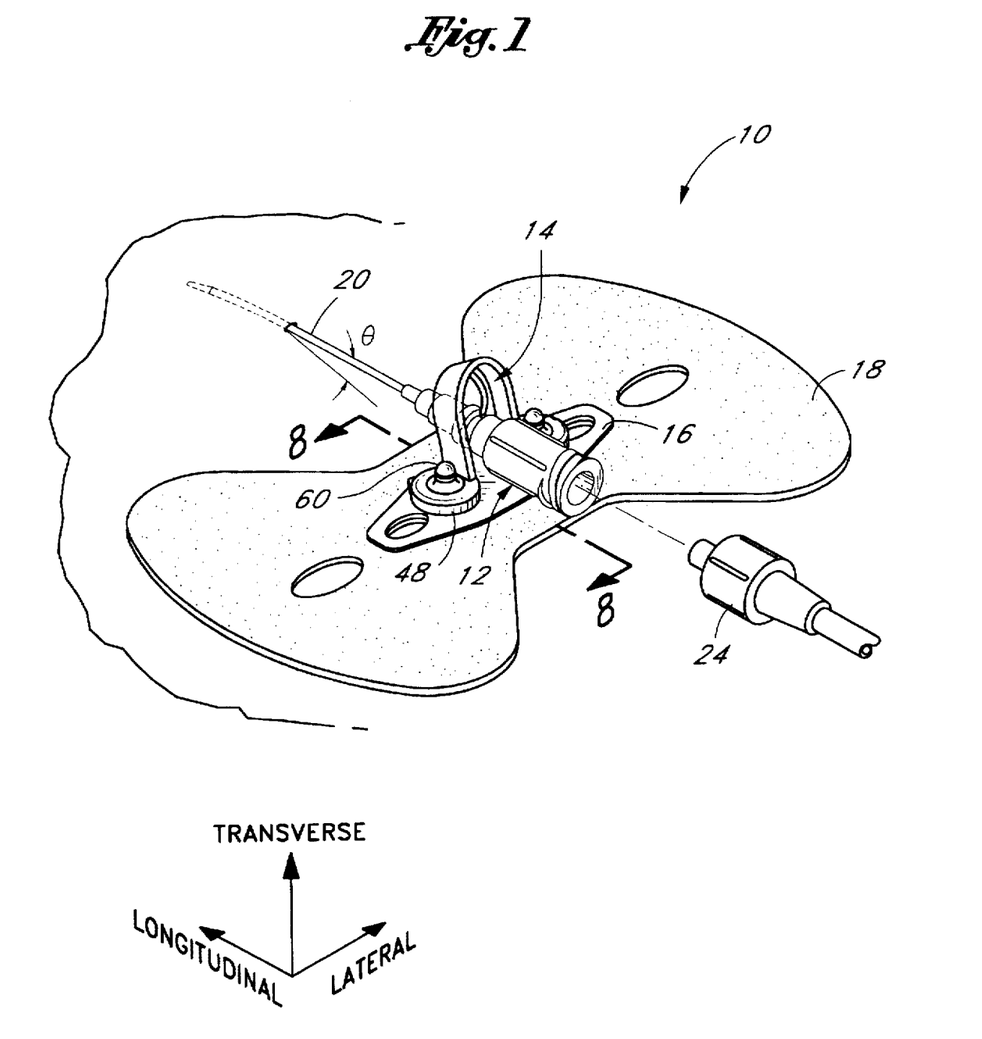
FIG. 1 is a perspective view of the catheter securement device retaining a catheter.

FIG. 1 illustrates a securement device 10 which is configured in accordance with a preferred embodiment of the present invention and is used in connection with an intraarterial catheter 12. It is understood, however, that the securement device 10 of the present invention also can be used with other types of catheters and catheterization devices (e.g., monitoring devices) utilized in a variety of different applications (e.g., arterial, intravenous, or epidural). The present securement device, however, is particularly well suited for use with catheters and catheterization devices which are position sensitive. As used herein, "catheter" means a catheter in all of its common usages, as well as any type of flexible tubing, wire, fiber or like delivery system designed to be inserted into a body channel, canal or cavity.

As seen in FIG. 1, a retainer 14 of the securement device 10 secures the catheter 12 while establishing an incident angle of the catheter 12. The retainer 14 also engages a base 16 which underlies the catheter 12. The base 16 in turn is mounted on an anchor pad 18 which is attached directly to the skin of the patient by means of a self-adhesive backing (not shown). Thus, by means of cooperation between the retainer 14 and the base 16, the catheter 12 is conveniently and painlessly anchored to the patient's skin.

Before describing the present securement device 10, an exemplary catheter 12 first will be described to assist the reader in understanding the illustrated securement device 10. As best seen in FIG. 1, the catheter 12 includes a cannula 20 which extends from a distal end of a hub 22 of the catheter 12. As used herein, "distal" and "proximal" are used in reference to the proximity of exemplary tubing 24 which commonly is attached to the catheter 12. The cannula 20 principally lies with a vessel (e.g., an artery) of a patient when in use. An angle formed between the cannula 20 and the skin of the patient is referred to as the catheter incident angle θ. As mentioned above, this angle θ varies from patient to patient depending upon the depth of the artery in the particular patient, and may change over time in an individual patient as the patient moves his or her wrist. It also may be advantageous to change the incident angle θ in order to improve the performance or function of a particular monitoring device used with the catheter 12.

The proximal end of the catheter hub 22 commonly includes a conventional luer-lock connector 26 to couple to catheter 12 to the tubing 24. The hub 22 also includes a grip cylinder 28 located adjacent to the luer-lock connector 26. A health care provider can hold and manipulate the catheter hub 22 at the grip cylinder 28.

Figure 2:
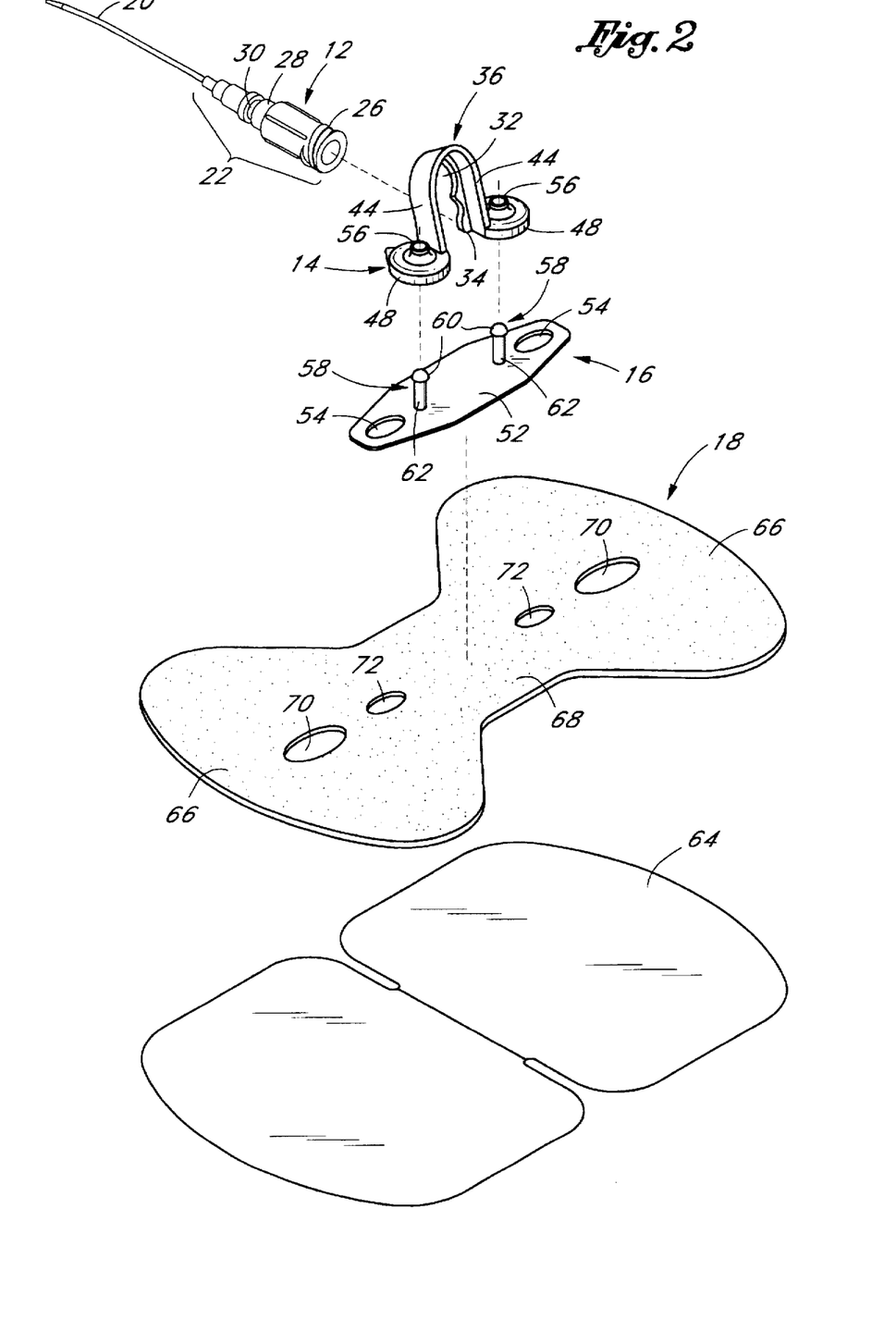
FIG. 2 is an exploded perspective view of the catheter securement device of FIG. 1.

As seen in FIG. 2, the conventional hub 22 includes an annular suture groove 30 between the grip cylinder 28 and the proximal base of the cannula 20. In the illustrated embodiment, the annular groove 30 circumscribes the catheter hub 22.

The individual components of the securement device 10 will now be described in detail. To assist in the description of the components of the securement device 10, a coordinate system has been provided. FIG. 1 illustrates a longitudinal axis, a transverse axis, and a lateral axis in relation of the catheter securement device 10. The longitudinal axis extends in a direction generally parallel to an axis of the catheter 12. The lateral axis lies perpendicular to the longitudinal axis within the plane of the base 16. The transverse axis extends transverse to the longitudinal and lateral axes. Additionally, as used herein, "the longitudinal direction" refers to a direction substantially parallel to the longitudinal axis. "The lateral direction" and "the transverse direction" are in reference to the lateral axis and transverse axis, respectively.

With reference to FIG. 2, the retainer 14 includes a slot 32 which extends generally in the transverse direction away from the base 16. The slot 32 is sized to receive a portion of the catheter hub 22 and is contoured to retain the catheter hub 22 at a plurality of transverse positions relative to the base 16. The catheter incident angle θ varies between the established positions, as described below.

The slot 32 advantageously has an arcuate shape curving in a direction out of a plane that is perpendicular to the longitudinal axis. The arcuate slot 32, as described below, desirably extends about the designed catheter insertion point.

Figure 3:
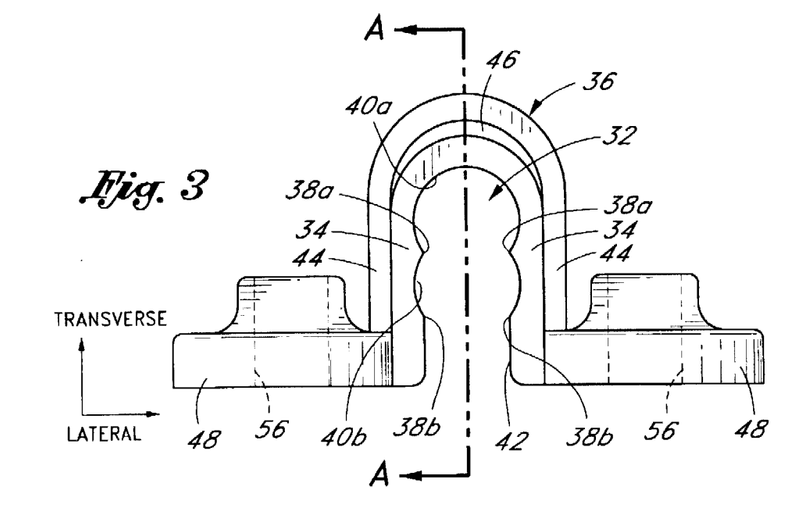
FIG. 3 is a proximal side elevational view of a retainer of the catheter securement device of FIG. 2.
Figure 4:
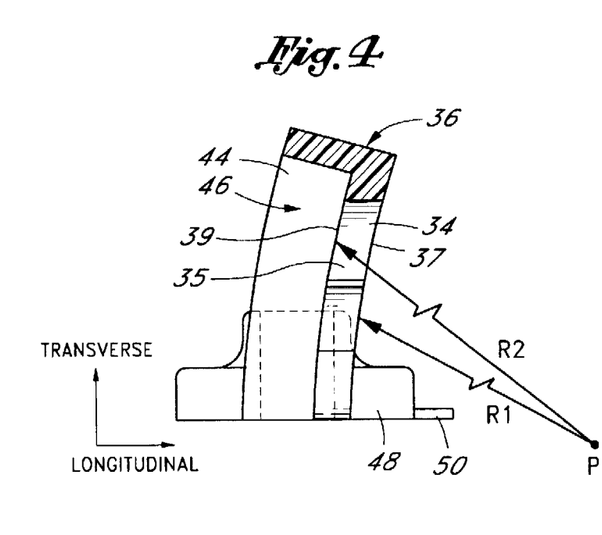
FIG. 4 is a cross-sectional, side elevational view of the retainer of FIG. 3 taken along line A—A.
Figure 5:
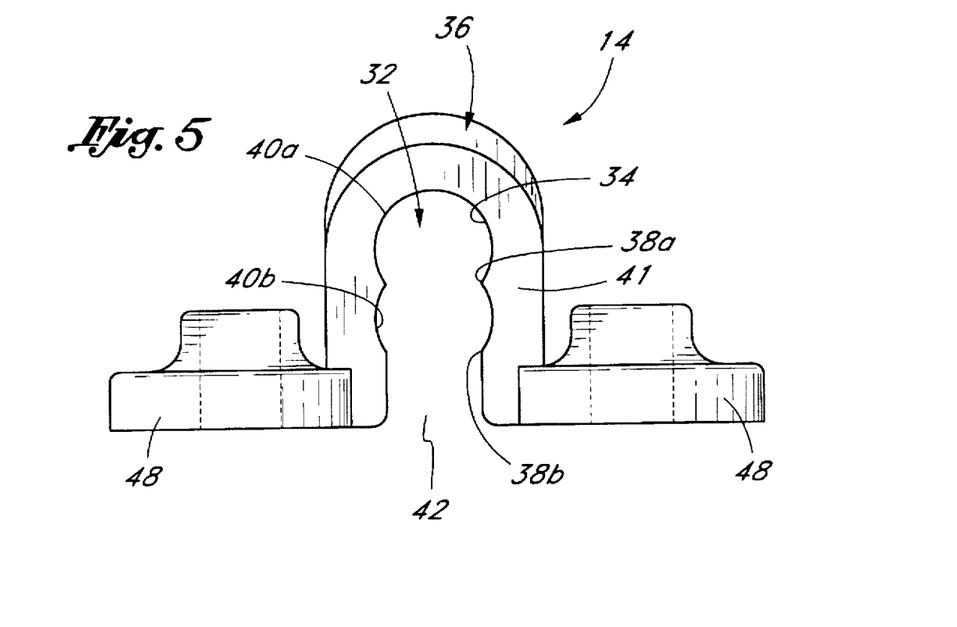
FIG. 5 is a distal side view of the retainer of FIG. 3.

The slot 32 desirably is defined between a pair of opposing rails 34 which cooperate with the suture groove 30 of the catheter hub 22. As best seen in FIGS. 3 through 5, the rails 34 have an arcuate shape with the opposing face 35 (see FIG. 4) of each rail 34 generally lying within a plane that is parallel to the longitudinal and transverse axes. A distal edge 37 of each rail 34 extends along an arc that is defined by a first radius $R_1$ having an origin at a point P distal of the retainer 14 and lying at a position in the transverse direction which normally would correspond to the surface of the patient's skin. The first radius $R_1$ generally corresponds to a typical distance between the catheter suture groove 30 and the insertion site of the catheter cannula 20.

A proximal edge 39 of each rail 34 also extends along an arc defined by a second radius $R_2$. The distal point P also serves as the origin for the second radius which larger than the first radius $R_1$.

The width of each rail 34 (i.e., the difference between the first and second radii $R_1$, $R_2$) is slightly smaller than the width of the annular groove 30 of the catheter hub 22. In particular, the width of each rail 34 is sized so as to allow the catheter hub 22 to slide without binding along the arcuate path defined by the rails 34 with the hub annular groove 30 receiving a portion of each rail 34. Minimum clearance, however, exists between each rail 34 and the walls of annular groove 30 in order to minimize longitudinal movement of the catheter 12 when secured within the retainer 14.

As seen in FIG. 3, the rails 34 have opposing protrusions 38 which project toward each other to decrease the spacing between the rails 34 (i.e., decrease the width of the slot 32 in the lateral direction). These protrusions 38 define positions of the catheter hub 22 within the slot 32 in the transverse direction, as described below.

In the illustrated embodiment, as that seen in FIG. 5, the rails 34 form a distal face 41 of an arch member 36. The slot 32 is defined in this distal face 41. Overlapping generally circular portions 40 define the contoured shape of the slot 32. An upper circular portion 40a gives the slot 32 a rounded upper end. The side rails 34 thus blend together at the upper end of the slot 32. As used herein, "upper" and "lower" are used in reference to the base 16. A lower circular portion 40b, positioned beneath the upper circular portion 40a, overlaps the upper circular portion 40a so as to define a first pair of opposing protrusions 38a on the side rails 34. At the center of the upper circular portion 40a, the slot 32 defines a first position of the catheter hub 22. The opposing protrusions 38a hold the catheter hub 22 within the upper circular portion 40a of the slot 32. The catheter 12 lies at a first incident angle with the catheter hub 22 resting in this first position in the upper circular portion 40a of the retainer slot 32.

The lower circular portion 40b may overlap with additional circular portions. The number of circular portions defines the number of positions of the catheter hub 22 within the retainer slot 32. In the illustrated embodiment, the slot 32 has only two circular portions 40a, 40b to define two positions of the catheter hub 22. Of course, the retainer 14 can have any number of circular portions 40 to define a variety of differing positions for the catheter hub 22 in order to suit a particular application.

The circular portions 40 desirably have the same diameters. Each circular portion 40 has a diameter which generally matches or is slightly smaller than the diameter of the hub 22 within the annular groove 30. The diameter of each circular portion 40, however, is smaller than the diameter of the hub 22 adjacent to the annular groove 30. In this manner, the annular groove 30 receives a portion of each side rail 34 when the catheter hub 22 is positioned within a circular portion 40 of the retainer slot 32.

The lowermost circular portion 40b overlaps with an entrance channel 42. The channel 42 has a width in the lateral direction which is smaller than the diameter of the catheter hub 22 within its the annular groove 30. The width of the channel 42 also is smaller than the diameters of the circular portions 40.

The intersections between the lowermost circular portion 40b and the channel 42 define a second set of protrusions 38b on the opposing rails 34. The second set of protrusions 38b are spaced from the first set of protrusions 38a so as to position the catheter hub 22 in a second transverse position within the lower circular portion 40b. In this position, portions of the rails 34 lie within the annular groove 30 of the catheter hub 22 to prevent longitudinal movement of the catheter 12. The cooperating sets of protrusions 38a, 38b on the rails 34 also prevent unintentional transverse movement of the catheter 12. The catheter 12 lies at a second incident angle with the catheter hub 22 resting at this second position within the lower circular portion 40b of the retainer slot 32.

As noted above, the illustrated retainer slot 32 includes only two circular portions 40a, 40b and therefore establishes only two incident angles for the attached catheter 12; however, the retainer 14 can be configured to define any number of positions to define a variety of incident angles for the catheter in order to suit a particular application. For conventional intraarterial applications, incident angles are generally set at one of two specific angles: 7.5° and 15°.

Thus, the two positions which the illustrated retainer 14 establishes correspond to these incident angles. With the catheter hub 22 positioned within the upper circular portion 40a of the retainer slot 32, the catheter 12 generally lies at a 15° incident angle. And with the catheter hub 22 positioned within the lower circular portion 40b of the retainer slot 32, the catheter 12 generally lies at a 7.5° incident angle.

Figure 6:
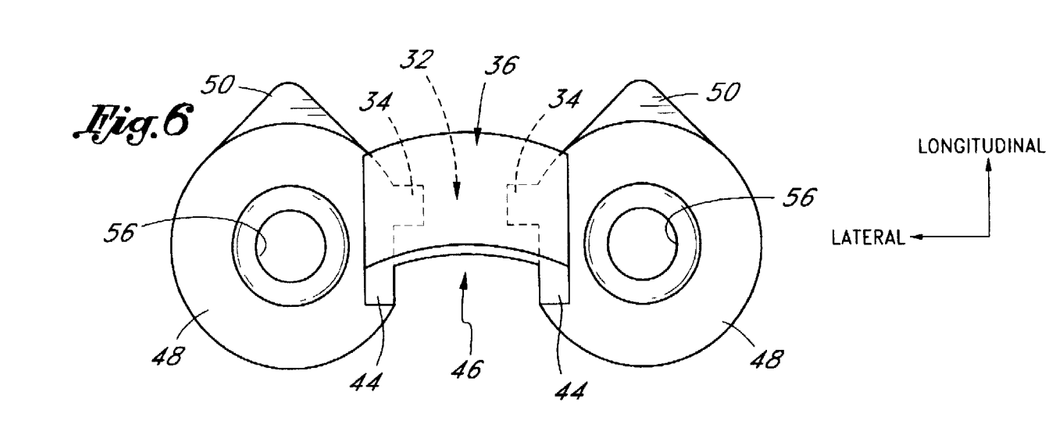
FIG. 6 is a top plan view of the retainer of FIG. 3.

As best seen in FIGS. 3 and 6, the arch member 36 includes a pair of side legs 44 to which the rails 34 are attached. The side legs 44 blend together at their upper ends to form the generally arched shape of the arch member 36. As seen in FIG. 4, each leg 44, and for that matter the entire arch member 36, also curves distally in a plane which is parallel to the longitudinal and transverse axes. That is, the legs 44 of arch member 36 follow the curve of the side rails 34 about the point P distal of the retainer 14. The radius of curvature of the distal end of the side legs 44 desirably matches the radius of curvature of the distal edges 37 of the side rails 34.

The retainer 14 can include indicia (not shown) on the side of the legs 44 to indicate the particular incident angle corresponding to each set position within the retainer slot 32. Alternatively, this information can be included on the anchor pad 18, as described below.

The arch member 36 also includes a relief 46 which lies adjacent to the rails 34 on the proximal side of the retainer 14, and between the side legs 44. The relief 44 is sized to receive without interference the portion of the catheter hub 22 proximal of the annular groove 30, with the hub 22 positioned at any position within the slot 32. For this purpose, as best seen in FIG. 4, the upper end of the relief 46 desirably is skewed relative to the plane of the base 16 by an angle at least equal to the catheter incident angle when the catheter hub 22 lies at its uppermost position within the retainer 14.

As seen in FIGS. 3 and 6, the retainer 14 also includes stabilizing platforms or feet 48 which rest on the base 16. In the illustrated embodiment, each foot 48 has a generally circular shape and is attached to one of the lateral side legs 44 of the arch member 36. The feet 48 desirably include locator tabs 50°. The tabs 50 lie on the distal side of the feet 48 and are generally formed in the shape of arrows.

Figure 7:
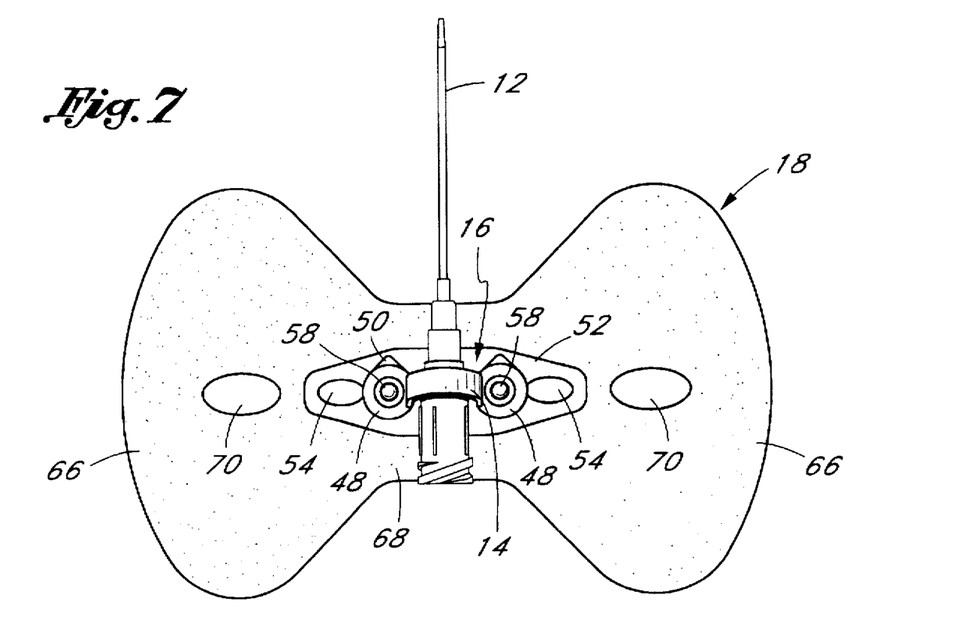
FIG. 7 is a top plan view of the catheter securement device of FIG. 1.

With reference to FIGS. 2 and 7, the base 16 includes a generally rigid planar member 52. In the illustrated embodiment, the planar member 52 has an elongated shape which extends in the lateral direction. The lateral ends of the planar member desirably are rounded and may include suture holes 54, as seen in FIG. 7.

The retainer 14 and the base 16 include interengaging structure to secure the retainer 14 to the base 16. In the illustrated embodiment, as best understood from FIGS. 1–3 and 8, each foot 48 of the retainer 14 includes a hole 56. The base 16 includes at least two posts 58 which project in the transverse direction away from the base 16. The posts 58 cooperate with the holes 56 in the retainer feet 48 to connect the retainer 14 to the base 16.

Figure 8:
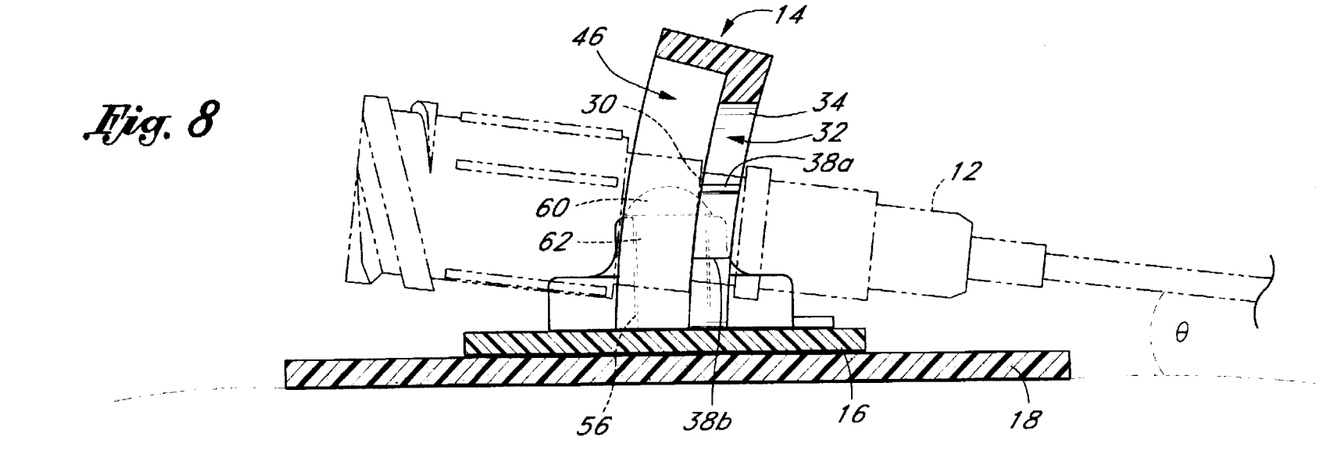
FIG. 8 is a cross-sectional, side elevational view of the catheter securement device of FIG. 1 taken along line 8—8 with the catheter positioned at a first incident angle.

Each post 58 includes a flared tip or head 60 and a neck or shank 62 which connects the head 60 to the planar base member 52. At least a portion of the head 60 is larger than the diameter of the shank 62. In the illustrated embodiment, the head 60 generally has a frusto-conical shape; however, it is understood that other shapes, such as, for example, barbs, spheres, hemispheres, mushrooms, and other types of radially projecting structures can be used as well. The head 60 also is larger than the diameter of the holes 56 in the retainer feet 48. The shape of the head 60 desirably allows it to be deflected when inserted through the corresponding hole 56 in the retainer foot 48, but resists retraction through the hole 56 when the head 60 lies above the retainer foot 48, as seen in FIG. 8.

As understood from FIG. 2, the posts 58 align with the holes 56 of the retainer feet 48 when the retainer 14 is properly positioned over the base 16. That is, the spacing between the posts 58 in the lateral direction generally matches the spacing between the holes 56 of the retainer feet 48 in the lateral direction. The posts 58 thus properly position the retainer 14 on the base 16 once they are inserted through the holes 56.

The retainer 14 and the base 16 can include other types of interengaging structure to secure the retainer 14 to the base 16. An example of interengaging structure, which provides a releasable interconnection between the retainer 14 and base 16, is a plurality of posts with extended tip or head portions and a plurality of slotted holes that are operable aligned with the posts to provide snap fit or friction fit engagement. Either component of the interengaging structure may be included on the retainer or the base. That is, if the retainer includes the posts, then the base includes the slotted holes, or if the retainer includes the slotted holes, then the base includes the posts. Each slotted hole is formed by a central circular opening, with at least one lateral slot or hole extending to one side. The slotted hole may have a central hole and two lateral holes extending to two opposite sides. Each post comprises a tip or head and a neck or shank which connects the tip or head to the retainer or base. The tip or head is larger than the diameter of the shank and may have any of a variety of shapes, such as, for example, a hemisphere, barb, sphere or mushroom shape. The tip or head is also larger than the diameter of the lateral hole of the slotted hole.

To provide snap fit or friction fit engagement, the posts are aligned with the slotted holes such that the tip or head of each post passes through the corresponding central hole. Then, the posts are slid laterally into the lateral slots where the slightly smaller diameter of the lateral slots compared to the diameter of the post necks provide a friction or snap fit engagement with the posts.

As with both the interengaging structure illustrated in FIG. 1 and the interengaging structure disclosed in the '024 application, the position of the posts and the holes can be reversed. That is, in the illustrated embodiment, the retainer 14 can include the posts 58 and the base 16 can include the holes 56.

The retainer 14 and the base 16 desirably are molded plastic components. The manufacture of these components can be accomplished by any of a variety of ways which will be well known to one skilled in the art. For instance, these components can be formed by injection molding using conventional medical-grade thermoplastics.

With reference to FIG. 2, the base 16 desirably is secured to the anchor pad 18 by means of cyanoacrylate, or other bonding material. The flexible anchor pad 18 comprises a laminate structure formed by an upper paper or other woven or non-woven cloth layer, an inner cellulose foam layer, and a bottom adhesive layer. Alternatively, the flexible anchor pad 18 may comprise an adhesive bottom layer and an upper cellulose foam layer. An upper surface of the foam layer is roughened by corona treating the foam with a low electric charge, as known in the art. The roughened or porous upper surface of the anchor pad 18 improves cyanoacrylate (other types of adhesive or bonding materials) adhesion when attaching the base 16 to the anchor pad 18.

A removable paper or plastic backing 64 (FIG. 2) desirably covers the bottom adhesive surface before use. The backing preferably resists tearing and is divided into a plurality of pieces to ease attachment of the pad 18 to the patient's skin. The backing desirably is split along a center line of the flexible anchor pad 18 in order to expose only half of the adhesive bottom surface at one time. The backing also advantageously extends beyond at least one edge of the anchor pad 18 to ease removal of the backing from the adhesive layer.

In an exemplary embodiment, the laminate structure of the anchor pad 18 is preferably formed by rolling a paper tape, such as a micro-porous rayon tape, available commercially as MICRO-PORE tape from 3M (Item No. 1530), over a medical grade polyvinyl chloride foam tape, such as that available commercially from 3M (Item No. 9777L). The foam tape preferably includes the bottom liner or backing. The anchor pad 18 is then stamped out of the laminated sheet of foam and paper. The backing forming the release taps, however, is not severed such that the tabs remain attached. The backing is then cut into two pieces along the center line of the pad 18 between the tabs.

In the illustrated embodiment, as best seen in FIG. 7, the anchor pad 18 includes a pair of lateral wing sections 66 which extend from a narrowed center section 68 of the anchor pad 18. The base 16 is attached to the center section 68. As a result, the lateral ends of the anchor pad 18 have more contact area to provide greater stability and adhesion to the patient's skin.

The lateral ends of the pad 18 also can include suture holes 70 which lies generally adjacent to the suture holes 54 defined in the planar base member 52. The pad 18 also includes hole 72 which corresponds with the suture holes 54 in the base 16. As seen in FIG. 7, the suture holes 54, 70 of the base 16 and the anchor pad 18 desirably have elliptical shapes with the major axes of the ellipses generally extending in the lateral direction.

The anchor pad 18 also may include indicia which indicates the proper orientation of the anchor pad 18 in reference to the catheterized cite and/or the incident angle corresponding to each transverse position of catheter hub 22 within the retainer 14. Such indicia can include, for example, arrows, words, icons, or other graphics. In one application, the indicia can indicate the direction of alignment with the indwelling catheter 12.

Figure 9:
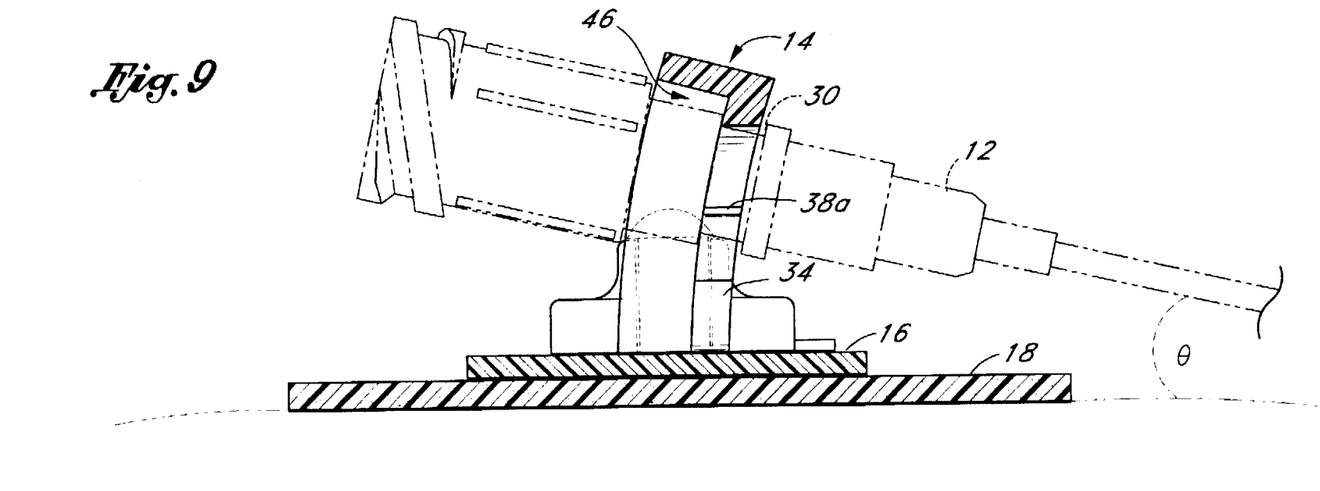
FIG. 9 is a cross-sectional, side elevational view of the catheter securement device of FIG. 1 taken along line 8—8 with the catheter positioned at a second incident angle.

The following discussion of the method of use will principally be in reference to FIGS. 1, 8 and 9, and will be discussed in the context of intraarterial catheterization of a peripheral artery. As will be readily appreciated by those skilled in the art, however, it is understood that the present securement device 10 can be adapted for use in other catheterization procedures as well. The discussion of the method of use is intended to augment the above description of the invention, and, thus, the following should be read in the context of the above description, and vise-versa.

A health care provider typically begins the catheterization process by positioning the catheter 12 at a desired location above a peripheral artery. The health care provider introduces a needle or other stylus through the cannula 20 of the catheter 12 and into the skin of the patient at a desired incident angle. For arterial use, the incident angle typically is between 7.5° and 15°. The health care provider then inserts the cannula 20 of the catheter 12 into the patient and withdraws the needle or stylus. The hub 22 of the catheter 12 remains exposed above the skin.

The health care provider removes the paper backing 64 which initially covers the adhesive bottom surface of the anchor pad 18, and attaches the pad 18 to the patient's skin proximate to the indwelling catheter 12. The health care provider desirably aligns the axis of the catheter 12 directly between the posts on the base 16. Light pressure over the upper layer assures good adhesion between the anchor pad 18 and the patient's skin. The anchor pad 18, due to its flexibility, conforms to the contours of the topical surface to which it adheres.

The health care provider then positions the annular groove 30 on the catheter hub 22 between the legs 44 of the retainer 14 and inserts the hub 22 into the retainer slot 32. The tabs on the retainer feet 48 desirably point toward the indwelling catheter 12 to indicate the proper orientation of the retainer 14 relative to the catheter 12. The rails 34 slide into the annular groove 30 and over the bottom surface of the groove 30. This act causes the side legs 44 of the arch member 36 to deflect slightly in the lateral direction until the catheter hub 22 sits within the lower circular portion 40b of the slot 32. In this position, as seen in FIG. 7, the walls of the annular groove 30 capture a portion of each rail 34 thereby preventing axial movement of the catheter 12 in the longitudinal direction. The proximal end of the catheter 12 lies within and extends beyond the relief 46 formed in the arch member 36 of the retainer 14.

The first and second pairings of protrusions 38a, 38b on the rails 34 grasp the hub 22 within the annular groove 30 to properly locate catheter hub 22 at the desired position. As mentioned above, this lower position within the retainer 14 is used with a low catheter incident angle, for example, 7.5°.

If a larger incident angle is desired, the health care provider moves the catheter hub 22 up within the retainer slot 32 to position the catheter hub 22 within a circular portion above the lowermost circular portion. In the illustrated embodiment, as seen in FIG. 9, the upper surface of the slot 32 and the first pairing of the protrusions 38a grasp the catheter hub 22 at the desired position. This upper position within the retainer 14 establishes a larger incident angle, for example 15°.

The health care provider attaches the retainer 14 to the base 16 by positioning the feet 48 of the retainer 14 above the posts 58 of the base 16 and aligning the posts 58 with the holes 56 in the retainer feet 48. The health care provider then forces the feet 48 over the posts 58 with the posts 58 inserting into the corresponding holes 56 in the retainer feet 48. The flared heads 60 of the posts 58 deflect until the feet 48 sit against the base 16. The flared heads 60 then return to an undeflected state, lying directly above an upper surface of the retainer feet 48.

The shape of the flared heads 60 prevents unintentional disengagement of the retainer 14 from the base 16. That is, the retainer feet 48 are not easily pulled off the posts 58. In order to remove the retainer 14 from the base 16, the health care provider snips off the heads 60 of the posts 58 so that the health care provider can easily lift the retainer 14 over the remaining shanks 62 of the posts 58. In the alternative, where a releasable connection between the retainer 14 and the base 16 is used, as described in application Ser. No. 08/316,024, the health care provider can disengage the retainer 14 from the base 16 in the manner described in that application.

At some stage during the above process or at the end of the process, the health care provider connects the tubing 24 to the proximal end of the catheter hub 22. The retainer 14 is configured so as not to interfere with this process even when the tubing 24 is connected to the catheter hub 22 with the retainer 14 already engaged.

If during the patient's treatment course it becomes desirably to adjust the incident angle of the indwelling catheter 12, the health care provider can do so by moving the catheter hub 22 within the retainer slot 32. Movement between positions (i.e., between circular portions) within the slot 32 causes the side legs 44 of the retainer 14 to deflect slightly outward in the lateral direction. The clearance between the shanks 62 of the posts 58 and the holes 56 of the retainer feet 48 allow for this limited lateral movement. Once the catheter hub 22 is positioned in an adjacent position, the legs 44 of the retainer 14 return to an undeflected state to capture the catheter hub 22 between the rails 34 in the desired position.

The present retainer 14 thus allows a health care provider to change the incident angle of the catheter 12 without disconnecting the catheter 12 from the retainer 14. Once set in a particular position, the retainer 14 fixes the catheter 12 at a desired incident angle. The retainer 14 also eliminates the use of tape and gauze to establish and secure the catheter 12 at a desired incident angle. The above-discussed disadvantages associated with tape and gauze thereby are eliminated. The retainer 14 further does not obstruct the view of the catheterization site, thereby allowing easy inspection of the site for contamination or infection.

Although this invention has been described in terms of a certain preferred embodiment, other embodiments apparent to those of ordinary skill in the art are also within the scope of this invention. Accordingly, the scope of the invention is intended to be defined only by the claims which follow.

What is claimed is:

1. A securement device for securing a catheter to a patient's skin, the catheter including a hub which has at least generally opposing slots that extend transversely to an axis of the catheter, said securement device comprising:

a base coupled to an adhesive surface and configured to receive a section of the catheter in a position in which the catheter section extends generally along a longitudinal axis; and a retainer coupled to said base by cooperating, interengaging structure between said base and said retainer, said retainer including a pair of opposing, arcuate rails which are spaced apart from each other in a direction generally parallel to a lateral axis, which lies perpendicular to the longitudinal axis and generally parallel to the base, the rails projecting away from said base in a direction that is generally normal to said base and generally parallel to a transverse axis, each rail extending along an arc defined within a plane which is positioned generally parallel to the longitudinal and transverse axes, each rail being sized to fit within a corresponding slot of the catheter hub, said rails including at least one pair of corresponding protrusions which project toward each other to decrease a distance between said rails, said distance between said protrusions being less than a distance between the slots of the catheter hub.

2. The securement device of claim 1 additionally comprising a pair of opposing side legs to which said arcuate rails are attached, said side legs blending together at one end to form an arch member.

3. The securement device of claim 2, wherein the arch member has an arcuate profile shape as viewed in a lateral direction, which is normal to the longitudinal and transverse directions.

4. The securement device of claim 1, wherein said retainer comprises an entrance channel into a space defined between the rails, said channel having a width in the lateral direction that is smaller than the diameter of the catheter hub.

5. The securement device of claim 2 additionally comprising a relief adjacent to said arcuate rails and between said side legs to receive a portion of the catheter hub proximal to the slot of the catheter hub.

6. The securement device of claim 1, wherein the opposing, arcuate rails are contoured to retain the catheter hub at a plurality of transverse positions relative to the base.

7. The securement device of claim 6, wherein said side legs include indicia to indicate an incident angle relative to the base obtained when the catheter hub is retained at a position between said arcuate rails.

8. The securement device of claim 1, wherein the cooperating, interengaging structure comprises a hole positioned in the retainer, and a post including at least one protuberance and extending from the base.

9. The securement device of claim 8, wherein the base includes at least two posts and the retainer includes at least two feet, each foot including the hole, and the spacing between the holes in the feet generally match the spacing between the posts of the base.

10. The securement device of claim 8, wherein the protuberance has a larger dimensional size, at least in one direction, than the hole, whereby the protuberance inhibits disengagement between the post and the hole.

11. The securement device of claim 1, wherein said adhesive surface is formed on a lower surface of an anchor pad which releasably attaches to a patient's skin, and the anchor pad has an upper surface to which said base is attached.

12. The securement device of claim 1 for use with a catheter hub including an annular groove circumscribing the catheter hub and being formed in part by the opposing slots, wherein said rails are sized to fit within the annular groove of the catheter hub.

13. The securement device of claim 1, wherein the rails are deflectable relative to each other to increase the distance between the rails.

14. The securement device of claim 1, wherein the protuberances are sized to contact and support the catheter hub at a transverse position above said base.

15. A securement device for securing an indwelling catheter to a patient's skin, the catheter including a hub, said securement device comprising a retainer having an arcuate slot sized to receive a portion of the hub, said slot extending in a transverse direction that is generally normal to the patient's skin with the retainer coupled to the skin of the patient and curving toward an insertion site of the indwelling catheter, said slot being contoured to define a plurality of position openings arranged to be capable of retaining the portion of the hub at a plurality of positions relative to the patient's skin, said position openings being located adjacent one another in the transverse direction.

16. The securement device of claim 15, wherein said arcuate slot contains a plurality of overlapping circular portions to receive a portion of the hub.

17. The securement device of claim 16, wherein said overlapping circular portions define at least two positions of the catheter hub within the retainer, each position defining an incident angle of the indwelling catheter when the catheter hub is retained in a circular portion.

18. The securement device of claim 17, wherein one position defines an incident angle of about 7° and another position defines an incident angle of about 15°.

19. The securement device of claim 15 additionally comprising a base detachably coupled to the retainer by interengaging elements.

20. The securement device of claim 19, wherein the interengaging elements comprise a post extending from the base, a hole formed in a foot of the retainer and sized to receive the post, and means for inhibiting unintentional retraction of the post from the hole.

21. The securement device of claim 19 additionally comprising an anchor pad supporting the base, the anchor pad including an adhesive lower surface for releasably attaching the anchor pad to a patient's skin proximate to the insertion site.

22. A securement device for securing an indwelling catheter to a patient's skin, said catheter including a hub, said securement device comprising a base coupled to an adhesive surface and a retainer coupled to said base by cooperating, interengaging structure between said base and said retainer, said retainer including means for retaining the hub of the catheter in at least a first position and a second position relative to the base with an incident angle of the indwelling catheter varying between said first and second positions, with the first position interposed between the base and the second position.

23. The securement device of claim 22, wherein said incident angle of the indwelling catheter varies between about 0° and 30°.

24. The securement device of claim 23, wherein said incident angle of the indwelling catheter varies between about 7.5° and 15°.

25. The securement device of claim 24, wherein said incident angle of the indwelling catheter is about 7.5° when the catheter hub is retained at the first position, and is about 15° when the catheter hub is retained at the second position.

26. The securement device of claim 22, wherein the cooperating, interengaging structure comprises a hole positioned in the retainer, and a post including at least one protuberance and extending from the base.

27. The securement device of claim 26, wherein the base includes at least two posts and the retainer includes at least two feet, each foot including the hole, and the spacing between the holes in the feet generally match the spacing between the posts of the base.

28. The securement device of claim 26, wherein the protuberance has a larger dimensional size, at least in one direction, than the hole, whereby the protuberance inhibits disengagement between the post and the hole.

29. The securement device of claim 22, wherein said adhesive surface is formed on a lower surface of an anchor pad which releasably attaches to a patient's skin, and the anchor pad has an upper surface to which said base is attached.

30. A method of adjusting an incident angle of an indwelling catheter comprising the steps of:

providing retainer having an arcuate slot which curves in a direction toward the insertion site of the indwelling catheter;

positioning a portion of a hub of the catheter within the slot;

securing the catheter hub in a first position within said slot to establish a first incident angle of the catheter;

sliding said catheter hub within said slot along the arcuate path defined by said slot to a second position without sliding the hub through the slot in a direction perpendicular to the slot; and securing said catheter hub in the second position within the slot to establish a second incident angle of the catheter.

31. The method of claim 30 additionally comprising securing said retainer to a base anchored to the skin of a patient.

32. The method of claim 31, wherein the sliding and securing the catheter hub from the first position to second position occurs while the retainer is secured to the base.

33. The method of claim 30, wherein securing the catheter hub in the first position establishes an incident angle of about 7° and securing the catheter hub in the second position establishes an incident angle of about 15°.

34. The method of claim 31, wherein securing involves aligning posts of said base with holes in feet of said retainer and interengaging said posts and feet.

35. A securement device for securing a medical line to a patient's skin at a plurality of incident angles, said securement device comprising a retainer including a slot that extends away from the patient's skin in a transverse direction with the retainer coupled to the skin of the patient, said slot having at least first and second sections lying adjacent to each other in the transverse direction, each slot section conforming to at least a portion of the medical line.

36. The securement device of claim 35, wherein the portion of the retainer in which the slot is defined has an arcuate shape.

37. The securement device of claim 35, wherein each slot section is configured to receive a fitting of the medical line.

38. The securement device of claim 37, wherein each slot section is configured to receive a portion of a catheter hub.

39. The securement device of claim 35, wherein the retainer includes at least one pair of corresponding protrusions which project toward each other to decrease a width of the slot, and said pair of protrusions being positioned between the first and second slot sections.

40. The securement device of claim 39, wherein the width of the slot between the pair of corresponding protrusions is less than a width of the medical line fitting.

41. The securement device of claim 35, additionally comprising a base detachably coupled to the retainer by interengaging elements.

42. The securement device of claim 35, wherein each section of said slot establishes a position of the medical line within the retainer, and each position corresponds to a preselected incident angle of the medical line relative to the base.

43. The securement device of claim 40, wherein the first slot section is configured to position the medical line at about a 7° incident angle when the medical line rests in the first slot section, and the second slot section is configured to position the medical line at about a 15° incident angle when the medical line rests within the second slot section.

44. The securement device of claim 41, wherein the interengaging elements comprise a post extending from the base, a hole formed in a foot of the retainer and sized to receive the post, and means for inhibiting unintentional retraction of the post from the hole.

45. The securement device of claim 41 additionally comprising an anchor pad supporting the base, the anchor pad including an adhesive lower surface for releasably attaching the anchor pad to a patient's skin.

46. The securement device of claim 35, wherein said first slot section is located closer to the patient's skin than the second slot section.

47. The securement device of claim 1, wherein the cooperating, interengaging structure comprises a hole positioned in the base, and a post including at least one protuberance and extending from the retainer.

48. The securement device of claim 3, wherein the cooperating, interengaging structure comprises a hole positioned in the base, and a post including at least one protuberance and extending from the retainer.

* * * * *